United States Patent
Yu

(12)
(10) Patent No.: US 6,502,983 B2
(45) Date of Patent: *Jan. 7, 2003

(54) MICRO-MACHINED THERMO-CONDUCTIVITY DETECTOR

(75) Inventor: Conrad Yu, Antioch, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/281,610

(22) Filed: Mar. 30, 1999

(65) Prior Publication Data

US 2001/0012313 A1 Aug. 9, 2001

(51) Int. Cl.[7] .............................................. G01N 25/18
(52) U.S. Cl. ......................................... 374/44; 374/43
(58) Field of Search ........................ 374/44, 43; 73/23.4, 73/25.03

(56) References Cited

U.S. PATENT DOCUMENTS

| | | | | |
|---|---|---|---|---|
| 3,683,671 A | * | 8/1972 | Van Swaay | 73/23.4 |
| 3,777,366 A | | 12/1973 | Kiefer | 29/592 |
| 4,471,647 A | * | 9/1984 | Jerman et al. | 73/23.4 |
| 4,741,198 A | * | 5/1988 | Farren et al. | 73/23.1 |
| 4,813,267 A | * | 3/1989 | Norem et al. | 73/23.4 |
| 4,918,974 A | * | 4/1990 | Hachey et al. | 73/23.4 |
| 4,935,040 A | | 6/1990 | Goedert | 55/197 |
| 5,177,696 A | * | 1/1993 | Bonne | 374/44 |
| 5,255,553 A | * | 10/1993 | Hale et al. | 73/25.03 |
| 5,295,389 A | * | 3/1994 | Nagata et al. | 73/25.03 |
| 5,297,868 A | * | 3/1994 | Graebner | 374/44 |
| 5,377,527 A | * | 1/1995 | Kamiunten | 73/25.03 |
| 6,019,505 A | * | 2/2000 | Bonne et al. | 374/44 |

FOREIGN PATENT DOCUMENTS

EP     0 724 151 A1     7/1996

OTHER PUBLICATIONS

Conrad Yu, "High performance hand–held gas chromatograph," Proceedings of the 1998 ASME International Mechanical Engineering Congress and Exposition, Nov. 15–20, 1998, pp. 481–486.

Stephen C. Terry et al, "A Gas Chromatographic Air Analyzer Fabricated on a Silicon Wafer," IEEE Transactions on Electron Devices, US, IEEE Inc., New York, vol. Ed–26, No. 12, Dec. 1, 1979.

* cited by examiner

*Primary Examiner*—Diego Gutierrez
*Assistant Examiner*—Yaritza Guadalupe
(74) *Attorney, Agent, or Firm*—L. E. Carnahan; Alan H. Thompson

(57) ABSTRACT

A micro-machined thermal conductivity detector for a portable gas chromatograph. The detector is highly sensitive and has fast response time to enable detection of the small size gas samples in a portable gas chromatograph which are in the order of nanoliters. The high sensitivity and fast response time are achieved through micro-machined devices composed of a nickel wire, for example, on a silicon nitride window formed in a silicon member and about a millimeter square in size. In addition to operating as a thermal conductivity detector, the silicon nitride window with a micro-machined wire therein of the device can be utilized for a fast response heater for PCR applications.

7 Claims, 2 Drawing Sheets

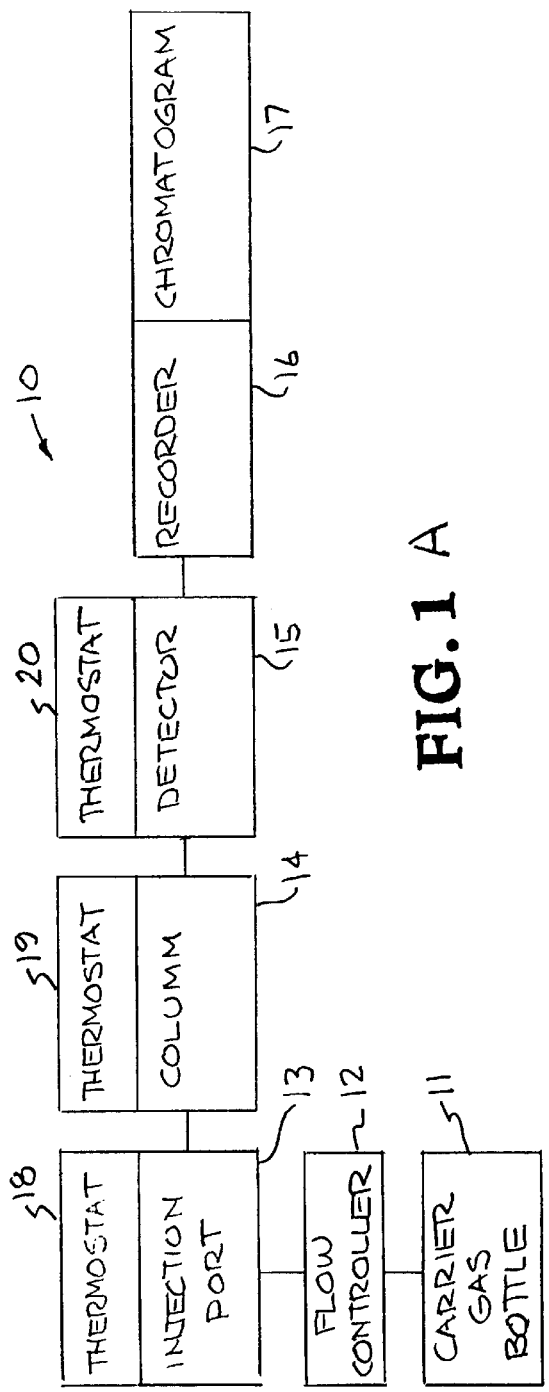
FIG. 1A
FIG. 1B
FIG. 1C

MICRO-MACHINED THERMO-CONDUCTIVITY DETECTOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to detectors, particularly to detectors for portable gas chromatography, and more particularly to a highly sensitive, fast response time micro-machined thermal conductivity detector utilizing a micro-machined wire on a silicon nitride window about a millimeter square in size.

In recent years, substantial effort has been directed to the development of small, portable gas chromatography systems to enable rapid response time for the detection and composition determination of various materials, such for example, as materials spilled on a highway. Portable gas chromatography systems include a carrier gas supply and control, sample gas injection means, one or more gas chromatographical columns, a detector, a recorder, and a readout, such as a chromatogram. Thus, miniaturization of the various components of the overall system have been undertaken to reduce the overall weight of the system to enable ready portability.

Recent efforts involving micro-machining of silicon gas chromatographic columns has enabled the construction of portable systems capable of testing various samples simultaneously. For example, a gas chromatograph on a silicon chip was accomplished in the early 1970s, wherein the major components (injector, separation column, and detector) were all formed on one silicon wafer, and the separation consisted of square channels anodically bonded between glass and silicon. See S. C. Terry "A Gas Chromatography System Fabricated on a Silicon Wafer Using Integrated Circutechnology", Ph. D. dissertation, Department of Electrical Engineering, Stanford University, Stanford, Calif., 1975; and S. C. Terry et al "A Gas Chromatograph Air Analyzer Fabricated on a Silicon Wafer", IEEE Trans. Electron Devices, Vol. ED-26, p. 1880, 1979. Since those early efforts, miniaturization efforts have been carried forward so as to result in a hand-held gas chromatograph, wherein the three above-referenced major components are fabricated separately utilizing silicon micro-machining techniques. See UCRL-JC-129689 Abs, "A Hand-held Gas Chromatograph", Conrad Yu et al, 1998. In a portable gas chromatograph, the size of gas samples is in the order of a nanoliter, thus the thermal conductivity detector needs to be highly sensitive and with fast response time.

The present invention satisfies the need in portable gas chromatography for a thermal conductivity detector that is highly sensitive and has fast response time. These features are achieved through a micro-machined detector wherein a silicon nitride window about one millimeter square in size is formed in a silicon member and provided with a micro-sized conductive wire, such as nickel (Ni), which is in contact with the sample gas and a carrier gas, such as helium (He).

SUMMARY OF THE INVENTION

It is an object of the present invention to provide a thermal conductivity detector for a portable gas chromatograph.

A further object of the invention is to provide a micro-machined thermal conductivity detector.

A further object of the invention is to provide a thermal conductivity detector which utilizes an electric element on a silicon nitride member, which can also be used as a heater.

Another object of the invention is to provide a thermal conductivity detector that is highly sensitive and has a fast response time.

Another object of the invention is to provide a detector which includes a silicon nitride window with a resistor formed thereon of a resistive metal conductor with a high temperature coefficient, and high temperature chemical stability under ambient conditions.

Another object of the invention is to provide a thermal conductivity detector having a structure which will hold a high temperature gradient and where most of the thermal energy is conducted away through gases passing therethrough.

Another object of the invention is to provide a micro-machined detector having a high thermal conductivity structure composed of silicon (Si) with a silicon nitride window containing a resistor composed, for example, of nickel (Ni) or tungsten (W), whereby the detector has high sensitivity and fast response time.

Other objects and advantages of the invention will become apparent from the following description and accompanying drawings. Basically, the invention involves a micro-machined thermal conductivity detector. The detector of this invention is particularly applicable for use with a portable gas chromatograph, wherein size of the gas samples is in the order of a nanoliter. The thermal conductivity detector of this invention is highly sensitive and with a fast response time, and this is compatible with small (hand-held) portable gas chromatographs. The high sensitivity and fast response time are achieved through a micro-machined silicon structure which includes a silicon nitride window about one millimeter square in size and on which is deposited a resistive conductor or resistor composed of metal, such as nickel or tungsten. The resistor patterned on a silicon nitride membrane may also be utilized as a heater for PCR applications.

BRIEF DESCRIPTION OF THE DRAWINGS

The accompanying drawings, which are incorporated into and form a part of the disclosure illustrate embodiments of the invention and, together with the description, serve to explain the principles of the invention.

FIGS. 1A, 1B and 1C are a schematic illustrations of a component layout of an embodiment of a small, portable gas chromatographic system, with the column and detector shown in enlarged cross-section in FIGS. 1B and 1C, in which the detector assembly of the present invention may be utilized.

DETAILED DESCRIPTION OF THE INVENTION

Figure 2:
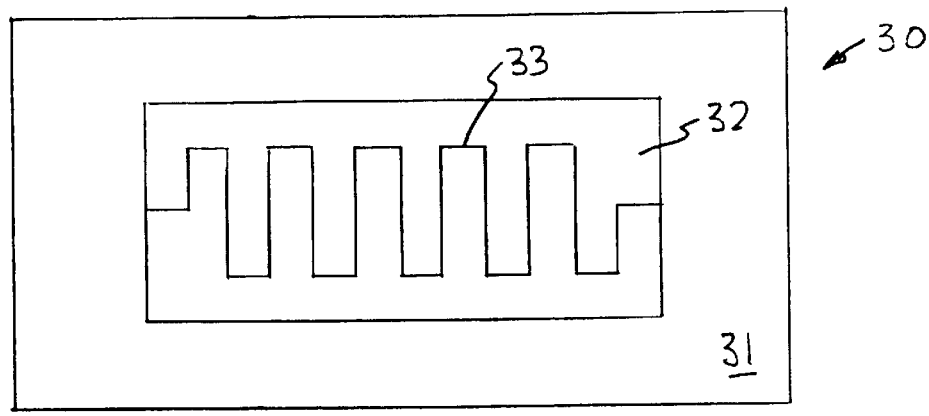
FIG. 2 is a greatly enlarged view of a detector assembly made in accordance with the present invention.

The present invention is directed to a thermal conductivity detector for small, portable gas chromatography wherein the size of gas samples is in the order of nanoliters. The detector of this invention is highly sensitive and has fast response time. The thermal conductivity detector utilizes a resistor composed of a resistive metal conductor, such as nickel or tungsten, with a high temperature coefficient, and a high temperature chemical stability under ambient conditions. The resistor is mounted in a structure such as silicon, which will hold a high temperature gradient and where most of the thermal energy is conducted away through gases flowing through the structure. The structure includes a window of material, such as silicon nitride, in which the resistor is located. While silicon, in general, has a high thermal conductivity, silicon nitride does not. Thus, to fabricate a nickel, gold or tungsten resistor on a silicon nitride window, a very strong and low internal stress silicon window is required, and such a silicon nitride window has been developed, which is similar to that of FIG. 2.

The micro-machined thermal conductivity detector of this invention has applications in miniature gas chromatograph (GC) systems, such as the hand-held gas chromatograph illustrated in above-referenced UCRL-JC-129689 Abs, and the systems components layout thereof is schematically illustrated in FIG. 1A. As seen in FIG. 1A, the overall GC system, generally indicated at 10, includes a carrier gas bottle or supply 11, a carrier gas flow controller 12, a sample injection port assembly 13, a separation column assembly 14, a detector assembly 15, a recorder 16, a chromatogram 17, and three thermostats 18, 19 and 20, positioned in each of the assemblies 13,14 and 15. The separation column assembly 14 and the detector assembly 15 include enlarged cross-sections indicated at 21 and 22 as shown in FIGS. 1B and 1C.

As shown in FIG. 1B, the GC separation column 14 is of a spiral configuration completely fabricated in silicon with a circular cross section and uniform polymer coating. The smoothness of the column surface is measured to be less than 50 Å rms. With a conventional sample injector assembly 13 and a micro-machined thermal conductivity detector 15, a standard sample of $C_1$–$C_6$ was injected into the system and well separated peaks with high resolution were detected. See above-referenced UCRL-JC-129689 Abs.

As pointed out above, the first gas chromatograph on a silicon chip included the three major components on one silicon wafer, and the separation column consisted of square channels anodically bonded between glass and silicon. In the GS system of FIG. 1A, the three major components (assemblies 13, 14, and 15) are fabricated separately. To fabricate the spiral separation column 14, two mirror-image spiral masks were patterned on two separate silicon nitride coated silicon wafers, and after the images were developed and transferred to the nitride mask, an HF—$HNO_3$—$CH_3COOH$ etchant for isotropic etching was used to form two semi-circular channels on the separate silicon wafers. After the two silicon wafers were completed, a precise alignment of the wafers with micron accuracy was used, and thereafter heated to 1200° C. for several hours to permanently thermal bond the wafers together to form a smooth circular cross-section separation column. Since the present invention is not concerned with the details of the separation column, such has been broadly described and further details thereof are deemed unnecessary.

As pointed out in above-referenced UCRL-JC-129689 Abs, a small portable (hand-held) GC system requires a highly sensitive thermal conductivity detector which needs to be low in thermal mass and highly thermally insulated so that the heat is only carried away through convection of the laminal flow. This is achieved by the present invention and involved patterning an electrical resistor on a silicon nitride member located in a silicon structure. The detection sensitivity of a GC using the thermal conductivity detector was measured to be one part per million; and the detectable temperature variation is about one part per 10,000, since the heat (thermal energy) is carried away in the laminar flow passing through the detector.

If it is assumed that all the thermal energy (heat) from the thermal conductivity detector is conducted to a laminar flow and carried away, the relation can be described as:

$$C(T)*[dT/dx]$$

where C(T) is the thermal conductivity of the laminar flow, and dT/dx is the temperature gradient of the laminar flow side of the detector. The other side of the thermal conductivity detector is completely thermal insulated.

The input energy to the detector can be written as $V^2/R$, where V is the voltage applied and R is the resistance of the detector. Since the input energy will have to equal the outgoing energy, we have:

$$C(T)(\text{He})*[dT(N)/dx]=[C(T)\text{He}-dC(T)*\{dT(S)/dx]$$

where C(T)(He) is the thermal conductivity of the laminar flow of helium gas, dT(N)/dx is the normal temperature gradient, and dT(S)/dx is the temperature gradient for sample gas flows. It can be written dT(S)dx is equal to d(R)(N)+dT(N)/dx or dT(N)/dx+ddT/dx. The above equal becomes:

$$ddT/dx/dT(N)/dx=dC(T)/C(T)(\text{He})$$

here dx is constant and since sample molecules move much slower than helium molecules, their thermal conductivity can thus be negligible. It can be assumed for one part in a million sample molecules, dC(T)/C(T) is equal to $10^{\wedge}(-6)$. If T(N) equals 100 degrees Celsius, we have:

$$dT/T(N)=dC(T)/C(T)=10\hat{\ }(-6)$$

or $$dT=10\hat{\ }(-4)$$

The embodiment of the thermal conductivity detector uses a resistor made of nickel (Ni) wire. When its temperature increases by dT, its resistance increases by dR, thus:

$$dR=R(O)*\text{alpha (Ni)}*dT$$

where alpha (Ni) is the temperature coefficient of the nickel resistance (0.0069 per degree Celsius). Let R(O)=200 ohms, we have:

$$dR=R(O)*\text{alpha(Ni)}*dT=1.38*10\hat{\ }(-4)\text{ohm}$$

If the thermal conductivity detector is a part of a Wheatstone bridge, the voltage generated on the signal input is:

$$V(b)=2*V(b)*dR/[2*(2R(O)+dR]$$

where V(b) is the biased voltage on the Wheatstone bridge. Or, if the V(b) is 10 volts:

$$V(b)=V(b)*\text{alpha (Ni)}*dT/2$$

thus $$V(b)=3.45 \text{ microvolts}$$

this signal is amplified by $10^{\wedge}4$, and this signal will become 0.0345 volts.

In verification experiments, for a sample with about 100 parts per million, the signal size read of the screen was 1.5 volts, the noise level was about 0.05 volts. In other words, the calculated value was about a factor of 2 larger than the experimental value. The minimum signal can be detected from a sample with:

100/million*0.05 volt/1.5 volt=3.3 parts/million

From these experiments, it is quite obvious, by eliminating a low frequency oscillation through a.c. modulation or grating, the noise level can be improved and achieve a part per million resolution.

FIG. 2 illustrates a side view of an embodiment of the thermal conductivity detector of the present invention. The detector indicated generally at 30 is composed of a silicon structure 31, having a silicon nitride window or membrane 32 on which is formed a nickel wire resistor 33. By way of example, the silicon nitride window 32 may have a thickness of 2000 Å to 1 µm, and in this embodiment a length of 1 inch to 2 inches and width of about 50 µm. The nickel wire resistor 33 may be a thickness of 50 Å to 1 µm, width of about 50 µm, and length of 1 inch to 2 inches, with a resistivity of 330Ω to 180Ω. While not shown, the nickel wire resistor is operatively connected to a power supply and control mechanism as known in the art.

Figure 3:
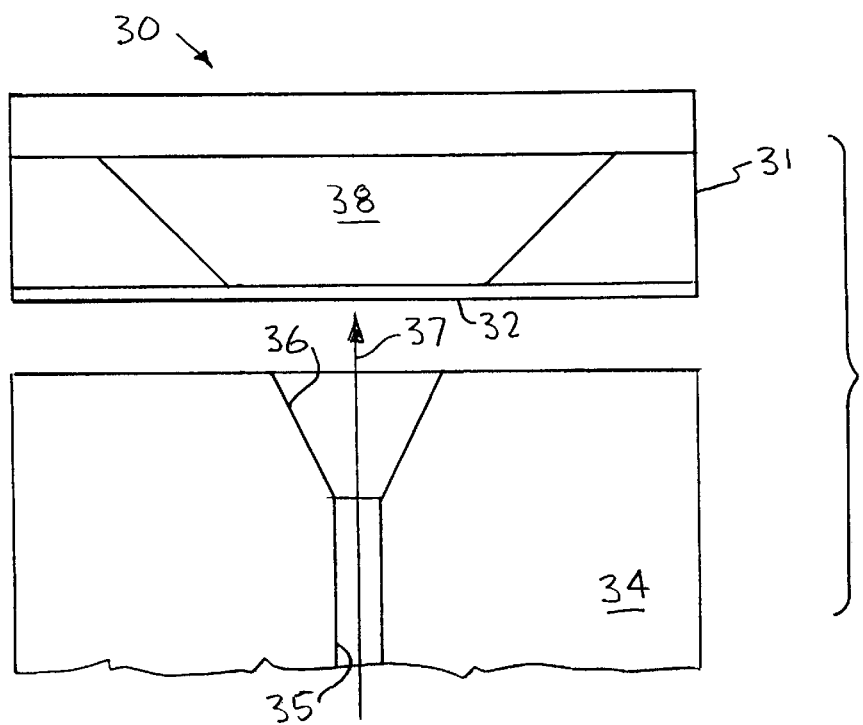
FIG. 3 illustrates, in an enlarged, exploded view, an embodiment of the detector of the present invention in combination with a separation column through which sample gas and carrier gas passes into the detector.

FIG. 3 illustrates an exploded view of the detector of FIG. 2 in combination with a sample separation column, with sample and carrier gases passing from the separation column into the detector. As shown, the detector 30 having a silicon nitride window 32 with a resistor therein, such as wire resistor 33 of FIG. 2, is positioned adjacent a separation column 34 having a micro-channel 35 extending therethrough, with micro-channel 35 provided with a tapered end 36. In actual practice, the detector 30 and the separation column 34 would be bonded together so as to prevent sample leakage therebetween. As indicated by arrow 37 a mixture of sample gas and a carrier gas, such as helium (He), passes through the micro-channel 35, tapered end 36, and through the silicon nitride window or membrane 32 into the interior 38 of the silicon structure 31 of detector 30. As described above with respect to FIG. 2, the window 32 is provided with an electrical resistor as known in the detector art, with the heat therefrom being carried away through convection of the laminar flow. Due to the use of the micro-machined thermal-conductivity detector with a resistor deposited on the silicon nitride window, high sensitivity and fast response time is obtained for gas samples having a size on the order of a nanoliter.

It has thus been shown that the present invention provides a thermal conductivity detector for use, such as in a portable gas chromatograph utilizing gas samples of the nanoliter size. The detector is highly sensitive and has a fast response time. Also, the window and wire resistor formed therein may function as a fast response heater for PCR applications.

While a particular embodiment of the invention has been illustrated and described, along with parameters and materials, to exemplify and teach the principles of the invention, such are not intended to be limiting. Modifications and changes may become apparent to those skilled in the art, and it is intended that the invention be limited only by the scope of the appended claims.

What is claimed is:

1. A thermal conductivity detector, comprising:
   a silicon structure having an opening therein,
   a membrane consisting of a single layer of silicon nitride without slits therein and having a cross-section of about one millimeter and a thickness in the range of about 1000 Å to 1 µm located in said opening, and
   an electrical resistor on a surface of the membrane constructed in the form of a wire having a width of about 50 µm and selected from the group consisting of nickel, tungsten and gold formed on said membrane.

2. The detector of claim 1, wherein said electrical resistor is composed of nickel.

3. The detector of claim 1, in combination with a portable gas chromatograph wherein the size of gas samples passing therethrough are in the order of a nanoliter.

4. The detector of claim 1, in combination with a sample separation column, wherein said structure of said detector is secured to said separation column such that sample and carrier gases passing through said separation column are directed through said membrane.

5. In a portable gas chromatograph, the improvement comprising:
   a highly sensitive, fast response time thermal conductivity detector,
   said detector including a single layer silicon nitride window without openings therein and about a millimeter square and having a thickness of about 1000 Å to 1 µm,
   said window being provided with an electrical resistor constructed of a resistive wire material selected from the group consisting of nickel, tungsten, and gold,
   said silicon nitride window being located in an opening of a silicon structure, whereby sample and carrier gases may pass through said window and carry away thermal energy produced by said electrical resistor.

6. The improvement of claim 5, wherein said resistive wire material is composed of nickel.

7. The gas chromatograph of claim 5, being constructed to utilize gas samples of a size on the order of a nanoliter.

\* \* \* \* \*